United States Patent
Zuegel et al.

(10) Patent No.: US 12,419,979 B2
(45) Date of Patent: Sep. 23, 2025

(54) PULSED ULTRAVIOLET IN-LINE STERILIZATION SYSTEM FOR PRIMARY DRUG CONTAINERS

(71) Applicant: Eyenovia, Inc., New York, NY (US)

(72) Inventors: James Zuegel, New York, NY (US); Peter Lam, New York, NY (US)

(73) Assignee: Eyenovia, Inc., New York, NY (US)

( * ) Notice: Subject to any disclaimer, the term of this patent is extended or adjusted under 35 U.S.C. 154(b) by 486 days.

(21) Appl. No.: 17/994,693

(22) Filed: Nov. 28, 2022

(65) Prior Publication Data

US 2023/0173118 A1     Jun. 8, 2023

Related U.S. Application Data (60) Provisional application No. 63/285,894, filed on Dec. 3, 2021.

(51) Int. Cl.
A61L 2/10     (2006.01)

(52) U.S. Cl.
CPC ............ *A61L 2/10* (2013.01); *A61L 2202/16* (2013.01); *A61L 2202/23* (2013.01)

(58) Field of Classification Search
CPC ..... A61L 2/10; A61L 2202/16; A61L 2202/23
See application file for complete search history.

(56) References Cited

U.S. PATENT DOCUMENTS

| | | |
|---|---|---|
| 5,786,598 A | 7/1998 | Clark et al. |
| 7,783,383 B2 | 8/2010 | Eliuk et al. |
| 8,125,333 B2 | 2/2012 | Ressler et al. |
| 2011/0155915 A1 | 6/2011 | Brueck et al. |
| 2012/0062840 A1 | 3/2012 | Ballou, Jr. et al. |
| 2012/0070467 A1 | 3/2012 | Ballou, Jr. et al. |
| 2012/0143152 A1 | 6/2012 | Hunter et al. |
| 2013/0150812 A1 | 6/2013 | Hunter et al. |

(Continued)

FOREIGN PATENT DOCUMENTS

| | | | |
|---|---|---|---|
| CN | 108939108 A | * 12/2018 | |
| JP | 2787724 B2 | * 8/1998 | ............ A61L 2/0011 |

OTHER PUBLICATIONS

English translation for JP 2787724 B2 (Year: 1998).*

(Continued)

*Primary Examiner* — Sean E Conley
(74) *Attorney, Agent, or Firm* — Mintz Levin Cohn Ferris Glovsky and Popeo, P.C.

(57) ABSTRACT

An in-line sterilization system including a caddie sized and shaped to releasably secure a container and a sterilization system for sterilizing the container using pulsed ultraviolet light. The sterilization system includes a first light source and a second light source positioned within an antechamber and forming a sterilization zone between the first and second light sources, each of the first and second light sources configured to transmit pulsed ultraviolet light into the sterilization zone. The sterilization system includes a transport system having a turntable. The perimeter region of the turntable is arranged to support the caddie upon receipt of the caddie within the antechamber and to move the caddie through the sterilization zone. The caddie and at least the perimeter region of the turntable are transparent to the ultraviolet light. Related systems, devices, compositions, and methods of use are provided.

12 Claims, 7 Drawing Sheets

(56) References Cited

U.S. PATENT DOCUMENTS

| | | |
|---|---|---|
| 2013/0172830 A1 | 7/2013 | Hunter et al. |
| 2013/0299607 A1 | 11/2013 | Wilkerson et al. |
| 2013/0334335 A1 | 12/2013 | Wilkerson et al. |
| 2014/0151457 A1 | 6/2014 | Wilkerson et al. |
| 2014/0336618 A1 | 11/2014 | Wilkerson et al. |
| 2020/0197218 A1 | 6/2020 | Newell et al. |
| 2020/0337896 A1 | 10/2020 | Ianchulev et al. |
| 2021/0177650 A1 | 6/2021 | Clauson et al. |
| 2022/0125631 A1 | 4/2022 | Ianchulev et al. |

OTHER PUBLICATIONS

English translation for CN 108939108 A (Year: 2018).*
U.S. Appl. No. 16/621,564, filed Dec. 11, 2019, US 2020-0197218.
U.S. Appl. No. 16/962,608, filed Jul. 16, 2020, US 2020-0337896.
U.S. Appl. No. 17/119,905, filed Dec. 11, 2020, US 20221-0177650.
U.S. Appl. No. 17/239,832, filed Apr. 26, 2021, US 2021-0398651.
U.S. Appl. No. 17/319,401, filed May 13, 2021, US 2021-0407663.
U.S. Appl. No. 17/397,874, filed Aug. 9, 2021 US 2022-0062035.
U.S. Appl. No. 17/434,711, filed Aug. 27, 2021, US 2022-0125631.
U.S. Appl. No. 17/704,395, filed Mar. 25, 2022, US 2022-0355329.
U.S. Appl. No. 17/849,425, filed Jun. 24, 2022, US 2022-0395221.
Brown et al. (1965) "The Preservation of Ophthalmic Preparations" J. Soc. Cosmetic Chemists, vol. 16:369-393.
Santvliet, L.V., et al. (2004). "Determinants of eye drop size." Survey of Ophthalmology, 49(2), 197-211. https://doi.org/10.1016/j.survophthal.2003.12.009.

* cited by examiner

PULSED ULTRAVIOLET IN-LINE STERILIZATION SYSTEM FOR PRIMARY DRUG CONTAINERS

CROSS-REFERENCE TO RELATED APPLICATIONS

This application claims the benefit of priority under 35 U.S.C. § 119(e) to Provisional Patent Application Ser. No. 63/285,894 filed Dec. 3, 2021. The disclosure of the provisional application is incorporated by reference in its entirety.

FIELD

The present technology relates generally to systems and devices for sterilizing primary drug containers for pharmaceutical use, more particularly using pulsed ultraviolet light for in-line sterilization.

BACKGROUND

Sterilization of primary containers in the pharmaceutical industry used subsequently during aseptic processing ensures the sterility of the finished product. Sterilization is achieved by exposing the primary container to a physical or chemical sterilizing agent. Physical sterilization techniques include dry heat, moist heat, and ionizing radiation. Chemical sterilizing agents include vaporized hydrogen peroxide (VHP), vaporized peracetic acid (VPA), Ethylene Oxide (EO), and the like.

Ultraviolet ("UV") light or radiation is used to control the growth of and bio-decontaminate microbial impurities in a variety of industries due to its purification, germicidal effects. UV-C, for example, is a short wavelength ultraviolet light that is germicidal, but is unable to pass through a variety of materials commonly used in large-scale pharmaceutical processing equipment.

SUMMARY

In an aspect, provided is an in-line sterilization system having a container with a reservoir portion defining an internal volume; a caddie sized and shaped to releasably secure the container; and a sterilization system. The sterilization system includes a first light source and a second light source forming a sterilization zone between the first and second light sources, each of the first and second light sources configured to transmit pulsed ultraviolet light into the sterilization zone; and a transport system having a turntable having a perimeter region configured to support the caddie and move the caddie through the sterilization zone. The reservoir portion, the caddie, and at least the perimeter region of the turntable are transparent to the ultraviolet light to sterilize the container prior to the internal volume being filled with a pharmaceutical.

The ultraviolet light can have a wavelength of between 200 nm and 400 nm. The system can further include a container-filling isolator and the sterilization system can be incorporated in-line and upstream of the container-filling isolator. The first light source can be positioned above the turntable and the second light source is positioned below the turntable. The caddie can be formed of cyclic olefin co-polymer. The perimeter region of the turntable can be formed of fused silica glass. The container can be formed of cyclic olefin co-polymer. The reservoir portion of the container can include a reservoir manifold sealed to a reservoir film. At least one of the reservoir manifold and the reservoir film can include cyclic olefin co-polymer. The caddie can include a nest formed in an upper surface of the caddie that is sized and shaped to mate with the reservoir portion of the container. The upper surface of the caddie further can include a surface feature sized and shaped to mate with a manifold coupled to the reservoir portion. The caddie can further include a latch configured to articulate relative to the upper surface of the caddie to secure the container within the nest.

In an interrelated aspect, provided is an in-line sterilization system having a caddie sized and shaped to releasably secure a container and a sterilization system. The sterilization system includes an antechamber; a first light source and a second light source positioned within the antechamber and forming a sterilization zone between the first and second light sources, each of the first and second light sources configured to transmit pulsed ultraviolet light into the sterilization zone; and a transport system. The transport system includes a turntable having a perimeter region, the perimeter region of the turntable arranged to support the caddie upon receipt of the caddie within the antechamber, the turntable configured to move the caddie supported on the perimeter region through the sterilization zone. The caddie and at least the perimeter region of the turntable are transparent to the ultraviolet light.

In some variations, one or more of the following can optionally be included in any feasible combination in the above methods, apparatus, devices, and systems. More details are set forth in the accompanying drawings and the description below. Other features and advantages will be apparent from the description and drawings.

Generally speaking, the figures are not to scale in absolute terms or comparatively, but are intended to be illustrative. Also, relative placement of features and elements may be modified for the purpose of illustrative clarity. It is to be understood that devices described herein may include features not necessarily depicted in each figure.

DETAILED DESCRIPTION

Described herein are systems, devices, and methods for sterilizing primary drug containers for pharmaceutical use.

The systems, devices, and methods described herein involve ultraviolet light for in-line sterilization. In some aspects, the primary drug containers are sub-assemblies of a device designed to deliver microdoses of a therapeutic, particularly ophthalmic formulations of a therapeutic to the eye (e.g., cornea) within a physiologic range of the tear film capacity using a uniform, collimated stream of micro droplets to coat an ocular surface.

The various features and functions of the systems, devices, and methods described herein may be applied to one or more devices described herein even though they may not be expressly described in combination. It should also be appreciated that various features and functions of the devices described herein can be applied to conventional devices and systems known in the art also useful for delivery of a medicament to the eye or other anatomy. Although the systems and devices are described in the context of ophthalmology medications and devices, this is not intended to be limiting. The systems and devices can be applied to any of a variety of primary containers useful for a variety of purposes and not limited to medicaments or to the eye.

System

Figure 1A:
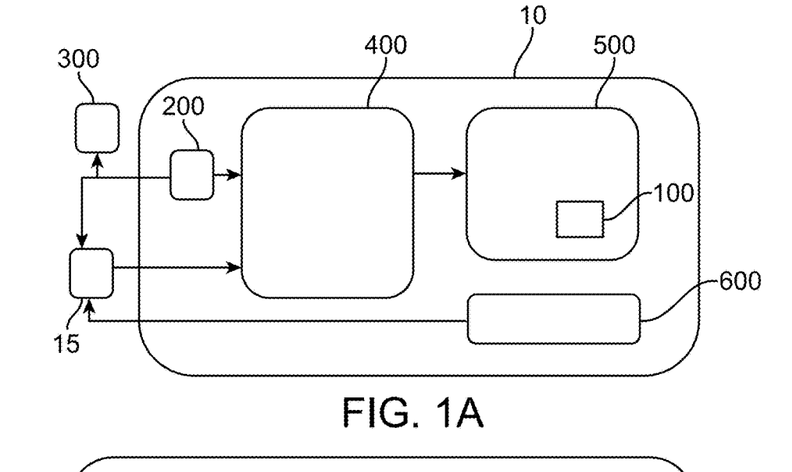
FIG. 1A is a box diagram of an implementation of a sterilization and fill system for primary containers.

FIG. 1A is a box diagram of a sterilization and fill system 10 for primary containers. The system 10 can include a container sterilization system 400 external to an isolator 500. The isolator 500 can provide ISO Class 5, Grade A space and can contain equipment 100 used to aseptically fill and finish a primary container 300. The sterilization system 400 is preferably a pulsed ultraviolet in-line sterilization (PUVIS) system. The sterilization system 400 can sterilize a container 300 held within a caddie 200 prior to filling the container 300 with a therapeutic within the isolator 500. The caddie 200 can provide accurate positioning of each individual container 300 so that the container 300 can be moved relative to the various systems (e.g., sterilization system 400, isolator 500, fill and finish equipment 100, post-chamber 600). The sterilization system 400 can be coupled on a first end of the isolator 500 and a post chamber 600 can be coupled to a second end of the isolator 500 for collecting filled drug containers 300 and caddies 200. In some implementations, the system 10 can incorporate a loading conveyor 15 to provide "no-touch transfer" of each caddie 200 loaded with a container 300 into the sterilization system 400. The containers 300 collected within the post-chamber 600 after filling can be assembled without aseptic processing into finished products, which can then be packaged and terminally sterilized. The caddies 200 can be returned by an operator or with the loading conveyor 15 to the sterilization system 400 to hold another container 300 for sterilization and filling. Each of these components will be described in more detail below.

The system 10 can be housed within a clean room (ISO Class 7, Grade C space). The system 10 has a generally small footprint (e.g., 6-8 feet long overall) so that the clean room may be similarly compact and efficient. Despite the small footprint, the system 10 is capable of high-volume production (e.g., 1 million/year/shift filled containers).

Isolator

Figure 1B:
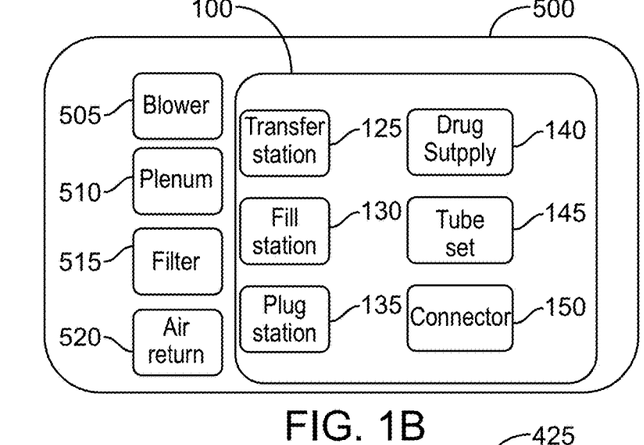
FIG. 1B is a box diagram of an implementation of an isolator of the sterilization and fill system of FIG. 1A.

FIG. 1B is a box diagram of an isolator 500. The isolator 500 can be any industry-standard hood for filling and plugging primary drug containers, such as a system used to provide ISO Class 5, Grade A space. The isolator 500 can include a blower 505, air supply plenum 510 to a high efficiency particle air (HEPA) filter 515, and HEPA air return inlets 520. The fill and finish equipment 100 can include a transfer station 125, fill station 130, plug station 135, sterile drug supply bag 140, and tube set 145. Caddies 200 with containers 300 can be manually transferred to automatic transfer stations 125. The stations 125 can accept the caddies/containers from the sterilization system 400 and transfer them to a fill station 130 and then to a plug station 135 and then manually transferred through the post chamber 600 to the end of the conveyor 15. Automated transfers can also be incorporated throughout the system 10. A sterile drug supply bag 140 can be used to fill the containers 300. The bag 140 can be a disposable, VHP-sterilized supply bag. Pre-sterilized disposable tube set 145 and connectors 150 can be used to fill the containers 300 still held by the caddies 200 within in the isolator 500. Non-disposable equipment may also be used for the sterile drug supply, tubing, connectors, etc.

Sterilization System

Figure 1C:
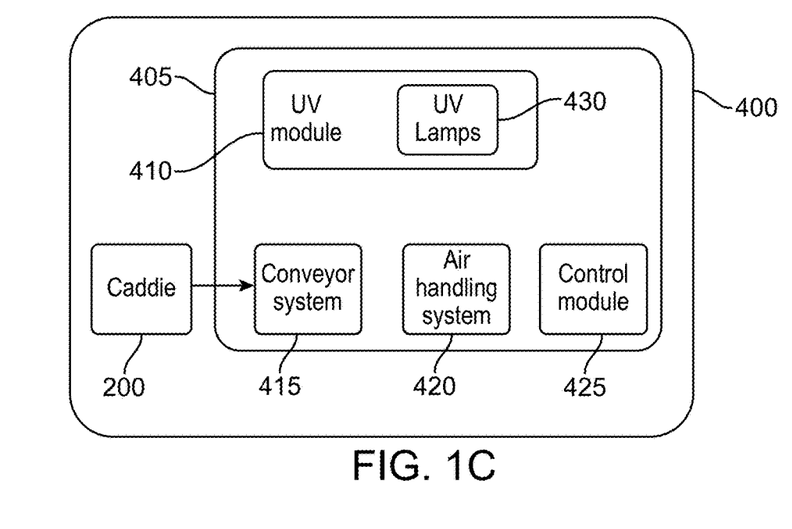
FIG. 1C is a box diagram of an implementation of a sterilization system of FIG. 1A external and upstream to the isolator of FIG. 1B.

FIG. 1C shows the sterilization system 400 that is external and upstream to the isolator 500 where the sterilized containers are subsequently filled. The sterilization system 400 can be coupled directly to a wall or chamber of the isolator such that the interior of the sterilization system 400 is separated from an interior of the isolator 500 by a partition. Empty containers 300 can be sterilized, sanitized, disinfected, or otherwise cleaned within the sterilization system 400 in preparation for filling the containers 300 within the isolator 500. The sterilization system 400 can include an antechamber 405 containing at least one pulsed UV lamp module 410, a conveyor or transport system 415, an air handling system 420, and a control module 425. The UV lamp module 410 can include two or more pulsed UV flash lamps 430. For example, the at least one pulsed UV lamp module 410 can include a first pulsed UV flash lamp 430 positioned at a first location relative to the sterilization system and a second pulsed UV flash lamp 430 positioned at a second location relative to the sterilization system forming a sterilization zone between the first and second lamps 430. As another example, the sterilization system 400 can include a first pulsed UV flash lamp module 410 positioned at a first location within the sterilization system antechamber 405 and a second pulsed UV flash lamp module 410 positioned at a second location within the antechamber 405 forming a sterilization zone between the first and second lamp modules 410. A single lamp module 410 having reflectors also can be used. Thus, where a system is described as having two pulsed UV flash lamps 430 it should be appreciated that the system can include a lamp module having a single lamp and one or more reflectors. The transport system 415 is configured to transport each caddie 200 holding a container 300 through the antechamber 405 into the isolator 500 while exposing each container 300 at least temporarily to the pulsed UV light from the lamp modules 410 in order to sterilize and decontaminate the container 300 prior to entering the isolator 500. The first and second lamp modules 410 can transmit pulsed ultraviolet light into the sterilization zone while the container 300 is moved through the zone. The UV sterilization of the containers 300 preferably occurs prior to filling the container within the isolator 500 because many drugs are UV sensitive. Each of these components will be described in more detail below.

The sterilization system 400 can be incorporated into an in-line (i.e., continuous or semi-continuous) process. For example, the transport system 415 of the sterilization system 400 can be incorporated immediately upstream of the container filling operation, wherein the transport system 415 delivers sterilized empty containers 300 to a container filling and finishing 100 operation. Sterilization can be accomplished within a short time, e.g., a matter of seconds per container. Each container 300 can be between the lamp modules 410 for less than 1 second. The caddie 200/container 300 and transport system 415 can be stopped in between the lamp modules 410 or pass slowly between the lamp modules 410. The transport system 415 can be adapted to transport containers 300 to and through the sterilization zone at a rate of up to about 30 containers per minute up to a rate of about 100 containers per minute or more, depending on the intensity and pulse length of the UV light of the lamp 430, the speed of the transport system 415, the length of the sterilization zone, etc. In some implementations, the transport system 415 can be at a rate about 10 containers per minute up to about 120 containers per minute or up to about 600 per minute. The maximum throughput rate can be controlled by the number of pulsed-UV flashes per minute. For example, if pulsed ultraviolet in-line sterilization takes 0.5 seconds per caddie/container and the caddie/containers can be indexed into position accurately, the maximum would be about 120 per minute. Likewise, if the pulsed ultraviolet in-line sterilization exposure takes about 0.1 second per caddie/container, the maximum would be about 600 per minute. The configuration of the transport system 415 can vary, but generally ensures that each container 300 held within a caddie 200 is transported through the sterilization zone in a consistent and repeatable manner.

In general, operations to sterilize the containers 300 may refer to operations to reduce the bioburden in and on the container 300 to be sterilized. Sterilizing may be intended to reduce active (e.g., living) bioburden to some degree. The disclosed sterilization may substantially disinfect or sterilize at least a portion of the container 300. Exemplary desired bioburden inactivation is greater than or equal to a 6 log reduction, (99.9999%), but could vary slightly from this. In some embodiments, at least 99.9999%, 99.99%, 99%, 95%, 90%, 80%, 75%, 70%, 60%, or at least about 50% of a particular biocontaminant may be killed or incapacitated. In some embodiments, between about 1 and 100% of a particular biocontaminant may be inactivated. Some systems may achieve, for example, at least about a 6 log reduction of a 2 mL container 300 and its caddie 200 within 0.5 seconds.

The mechanism of sanitizing the containers 300 may be through the exposure of ultraviolet radiation. This exposure may be delivered in pulsed wave form. In some implementations, the dose of ultraviolet radiation may include one or more pulses. The dose may include a timed exposure at a controlled power. The power may be controlled by modulation of current and/or voltage applied to the radiation source to substantially achieve the controlled radiation level, which may increase, decrease, and/or remain substantially constant during the dose time period.

In some embodiments, a controller may achieve time-varying or constant radiation level by modulation of optical path's transmission characteristics, such as by selecting which of a number of optical paths to use to couple the radiation from the source(s) to the container 300, and/or by modulating characteristics of the optical coupling (e.g., filtering) to couple more or less radiation from the source to the container 300. The radiation subjected to the container 300 is known as the delivered dose. The delivered dose includes an accumulated exposure value. In an illustrative example, a desired dose is one that is predetermined based on, for example, a desired accumulated exposure value at a specific energy density selected to be sufficient to inactivate one or more types of biocontaminants to a selected degree. In general, sanitization may involve, for example, reducing the number of viable microorganisms present.

Biocontaminants, known as the bioburden, may include, but are not limited to, viruses, bacteria, spores, fungi, molds, protozoa and yeasts, for example. In a range of examples, ultraviolet radiation may be used to kill one or more types of the biocontaminants on, around, or within portions of a container 300. Some embodiments may be beneficially applied to provide or enhance sanitization of containers 300 and/or associated equipment (e.g., handling equipment, including robotic manipulators), fluids (e.g., water), or other materials that may come into proximity and/or contact with containers 300 for which sanitization may be a concern.

The amount of UV time exposure required for sanitization is a function of the energy level received by the target at the required frequency spectrum. However, a predetermined exposure time for a dose may be based on other criteria. Both fixed and variable profiles may be executed at various levels of intensity, number, spacing, and timing. The outputs of UV sources may decay over time. Calibration and/or closed-loop control may be implemented by a processor, such as on a programmable logic controller or an embedded controller, to compensate such decay to maintain desired profiles (e.g., a predetermined accumulated dose of radiation).

The pulse frequency and pulse duration can be varied to create desired power. Exposure may be completed in less than 10 msec, up to about 1, 5, 10, 20, 30, 40, or up to at least about 60 seconds, for example. If pulsed, pulses may be delivered at a fixed or variable frequency of between about 0.01 Hz and about 1 kHz, such as between about 0.1 Hz and 100 Hz, or between about 2 Hz and about 10 Hz. Individual pulse duration may be less than one second, such as between about 1 ns and 100 ms, or between about 10 ns and 10 ms, or between about 100 ns and 1 ms, or between about 1000 ns and about 0.1 ms, such as between about 300 and 400 microseconds.

In an implementation, the voltage is between 1000 V up to about 3000 V, the pulse duration is between 100 μsec-7000 pec with off time between 10 msec up to about 6200 msec, and the exposure period is between 100 msec up to about 6200 msec. The maximum number of bursts during the period can be 6000. The pulse mode can be single, burst, or continuous.

In some implementations, the sterilization system 400 may include apparatus to focus or direct radiation supplied from each of the UV sources onto one or more selected regions or spots, or combine their output patterns using offsets to provide the desired illumination pattern at the target. UV sources may have non-uniform output patterns. By changing pattern centerlines, an aggregate output energy pattern that meets desired requirements can be generated. One example is to have multiple UV sources combined in such a manner as to provide a nearly uniform energy output over a much wider range than could be achieved with focusing the UV sources onto a single spot.

A UV source may include, for example, flash bulbs to produce very high peak energy levels, on the order of 1 J/cm2, or 10 J/cm2, or 30 J/cm2 in the UV-C band, which may include, but are not limited to, between 100 nm and 280 nm. In some examples, these are provided in very short bursts ranging from less than 1 ns to 100 ms at frequencies from about 0.01 Hz to about 1 kHz. Some pulsed bulbs may generate a wide band spectrum. In some embodiments, the UV light output may include a wider spectrum of radiation. For example, the pulsed UV light may include energy content in the VUV, UV-A, UV-B, and UV-C ranges, and may include some energy content at wavelengths shorter and/or longer than UV wavelengths, e.g., IR or visible light.

The wavelengths can include between 200 and 3000 nm, such as between about 160 and 380 nm, or between about 230 and 300 nm, or between about 250 and 270 nm, for example.

Energy delivered to the object to be sanitized may be a function of the number of pulses and the energy associated with each pulse. In some examples, a total energy delivered may be less than 1 Joule between about 1 Joule and about 20 Joules, up to about 30, 40, 70, 100, 250, 500, 600, 750, or at least about 1000 Joules. Over longer time spans, any practicable amount of energy may be delivered to achieve an effective and/or desired reduction in active bioburden, such as spores, bacteria, and/or viruses, for example.

UV sources, such as mercury vapor lamps, metal halide lamps and other constant wave sources generally provide energies in the range of about 1 mJ/cm2 to 400 mJ/cm2 in the UV-C band, or more. Packaged either singly or with multiple source packages to increase total power, such UV sources can provide suitable energy levels for sanitization in a specified time. Lower or higher energy levels may also be used depending on the sanitization time constraints.

UV sources, such as LEDs can be tailored to provide energy in very narrow bands including, for example, UV-C. Output spectrums can be tailored to provide total spectrums within, for example, ±500 nm, ±100 nm, ±10 nm or ±1 nm or less of the center band frequency of about 250-290 nm or 265-275 nm. This may advantageously affect heating, ozone production, and/or operator safety of the broader spectrum bulbs. LEDs and/or LED arrays in the power range of 1 mJ/cm$^2$ to 400 mJ/cm$^2$, or more, packaged either singly or with multiple source packages to increase total power and provide suitable energy levels for sanitization at high throughput for automated applications. Lower or higher energy levels may also be used depending, for example, on the sanitization time constraints. In an implementation, the ultraviolet light is delivered from a Xenon lamp in broad band UV wavelengths from 200 nm to 400 nm or from 200 nm up to about 1200 nm.

In various implementations, two or more UV LED sources may be placed at various locations distributed and directed to illuminate at least one surface to be sanitized. UV LEDs may be distributed in rectangular, linear, curvilinear, circular, spherical, or other patterns to expose one or more regions and/or surfaces to UV radiation. In various applications, predefined LEDs may be selected to operate at selected times to provide a dose of UV radiation. The dose and selection of which LEDs to activate and the timing of their activation may be determined according to the type and/or size of the object to be exposed. The LEDs can be activated in series, in parallel, overlapping or the like, and the timing of the activation often depends on the purposes to be achieved, such as high power, long duration with lower power, preserving source lifetime and more.

In some embodiments, the UV lamps in the sterilization system 400 may be cooled and/or cleaned by a flow of clean air with the air handling system 420. Such air flow may cool and/or substantially reduce particulate or organic solvents from depositing on the lamp surfaces. Connecting it to a low-pressure peripheral duct can force the air to be drawn into the UV lamp housing from just below the fan filter unit outlet (where it is cleanest) and to flow over the UV lamp to provide cooling. In some embodiments, such cooling may be performed without additional air moving elements that may generate air currents that may disrupt controlled laminar air flow patterns.

Example methods to deliver a required dose of ultraviolet radiation to a target may include continuous emission, intermittent emission, and pulsed emission. For continuous emission, suitable sources may require warm-up time and typically do not suit repetitive and/or frequent on-off cycles. Examples of such sources include, but are not limited to, mercury vapor lamps, fluorescent backlights, and metal halide lamps, and combinations of these and other sources. For intermittent emission, suitable sources can operate continuously and also have the capability of repetitive and/or frequent on-off cycles (e.g., LEDs, and lasers). For pulsed emission, suitable sources include the sources that are designed to flash at specified frequencies with specified pulse widths, such as flash bulbs using Xenon or other appropriate gases. Pulsed UV light provides a high intensity over a short period of time. High power bursts can create the desired sterilizing effect as well as allow samples being sterilized to cool/dissipate heat in between pulses. Higher power penetrates materials and sterilizes the inside surfaces. Continuous emission UV light can also be used. In some implementations, the continuous emission UV light can be used to sterilize the surfaces inside the antechamber 405 or another surface that does not require penetration and therefore does not require as high power.

Figure 2:
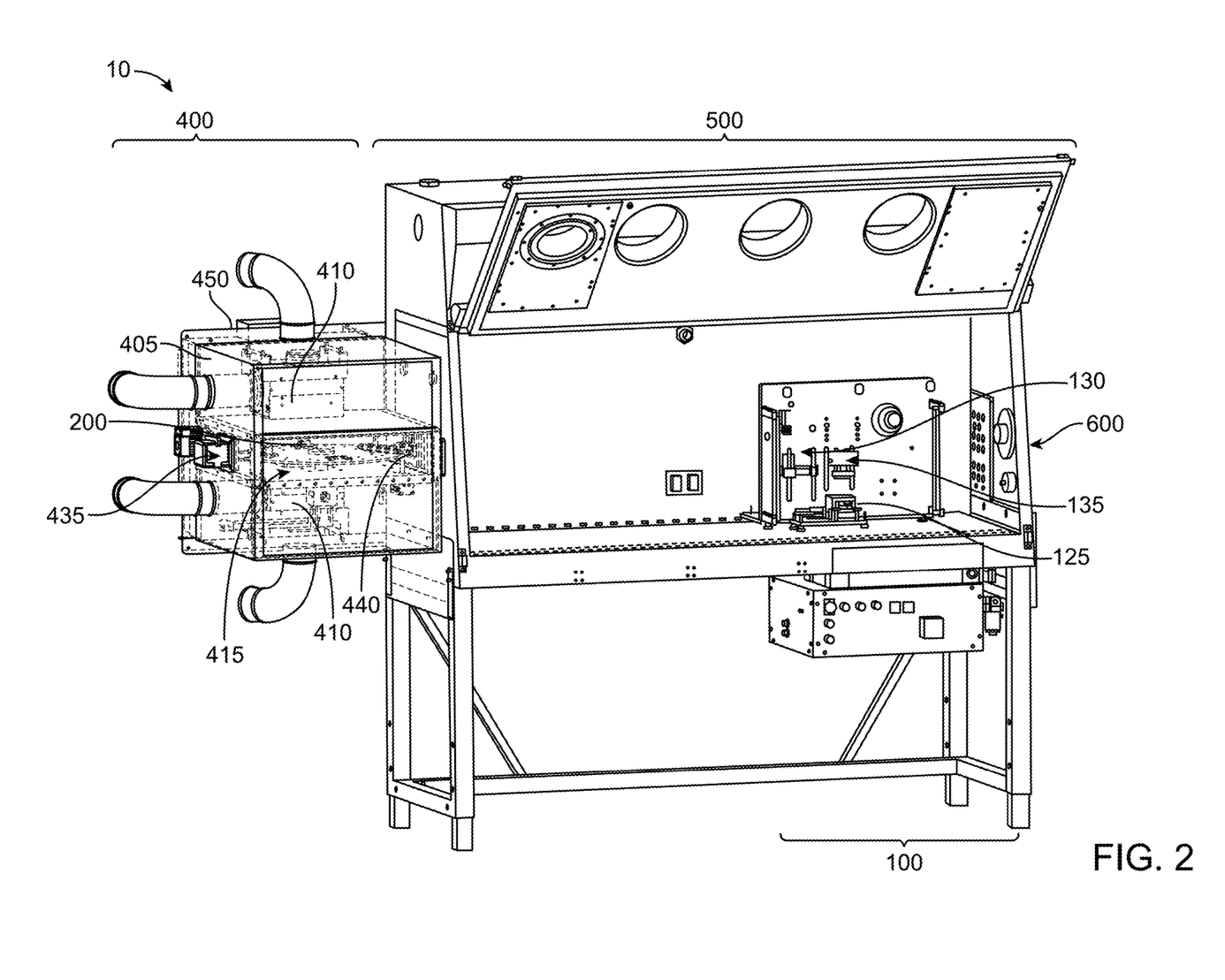
FIG. 2 is a perspective, partial view of an implementation of a sterilization and fill system for primary containers.
Figure 3:
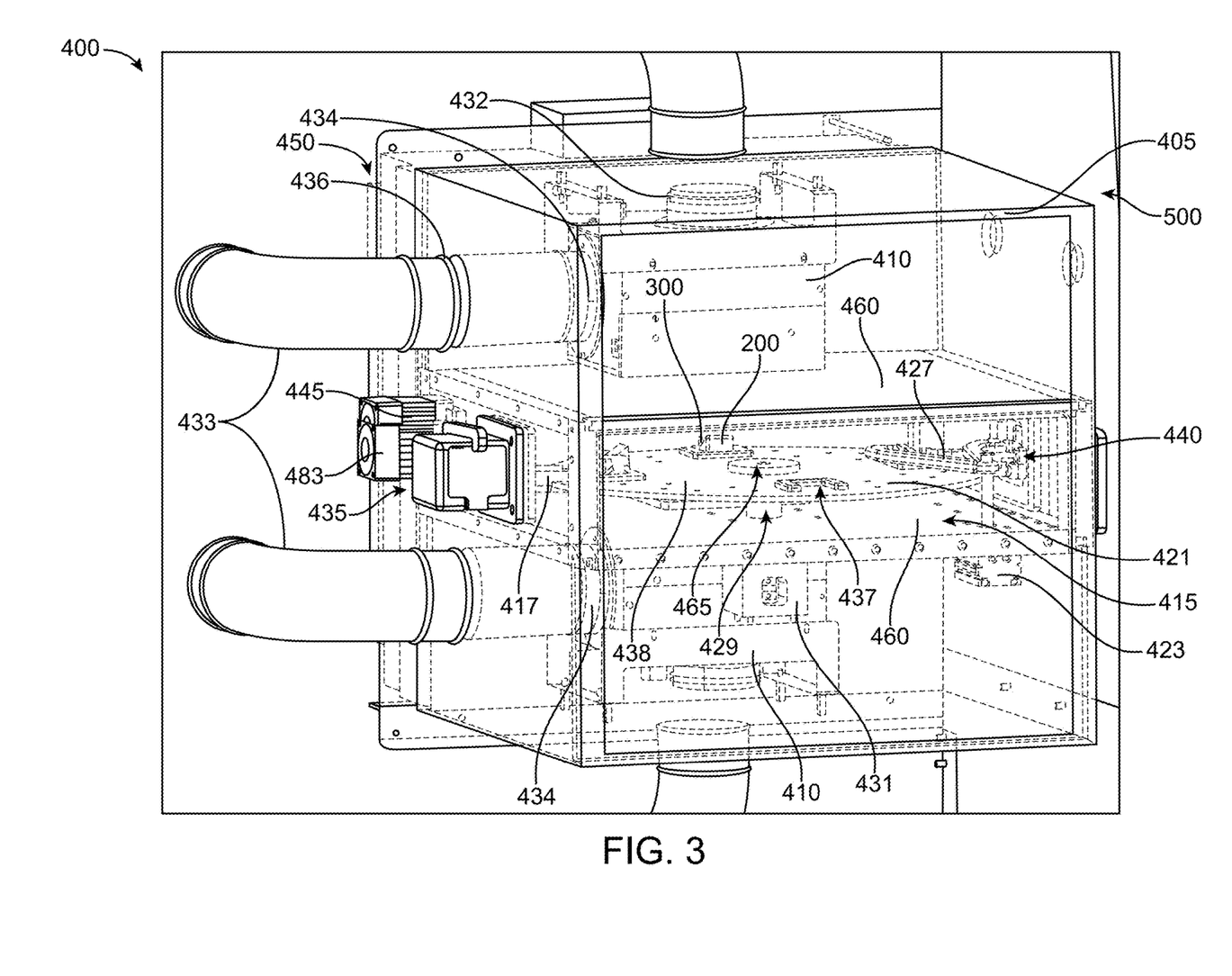
FIG. 3 is a perspective, partial view of the sterilization system of FIG. 2.

FIGS. 2 and 3 show an implementation of the antechamber 405 of the sterilization system 400, which can be a stainless steel container configured to be coupled to a wall of a standard isolator 500. The antechamber 405 can be fabricated from other materials so long as it is effective in filtering/shielding the UV light rays produced therein to protect operators from exposure. The sterilized containers 300 can be fed from the antechamber 405 of the sterilization system 400 into the isolator 500 for filling and finishing. The antechamber 405 can include independently actuated inlet door 435 and outlet door 440 for passing the caddies 200 into and out of the antechamber 405. The antechamber 405 can incorporate safety interlocking with the isolator 500. For example, the inlet door 435 for passing the caddie 200 holding a non-sterile container 300 from the cleanroom into the antechamber 405 can be opened while the outlet door 440 separating the interior of the antechamber 405 and the isolator 500 is closed. UV radiation from the UV lamps 430 can be substantially contained within the antechamber 405. Both the inlet door 435 and the outlet door 440 can be closed during sterilization of the container 300 with the pulsed-UV light. The inlet door 435 can be closed and the outlet door 440 can be opened with the sterilized container 300 is transferred into the isolator 500. In an implementation, the antechamber 405 can include an interlock that disables the UV light source until a portion of the container 300 is in the antechamber 405 such that a substantially complete light seal is formed to prevent substantial light from escaping. In some implementations, the antechamber 405 can be fitted with glovebox access. The antechamber 405 may also incorporate a camera 445 to allow remote monitoring of processes. The camera can detect whether the containers 300 are properly oriented on the turntable 421 or whether there are any irregularities in the position of each container 300 moving through the antechamber 405. The camera 445 can be a CCD with night vision or IR illumination with a glass lens.

Again with FIGS. 2 and 3, the antechamber 405 of the sterilization system 400 can include at least one and preferably at least two UV lamp modules 410. The UV lamp modules 410 can be directed towards a container 300 positioned within a caddie 200 on the transport system 415 within the antechamber 405 from opposing directions thereby forming a sterilization zone or exposure tunnel through which the transport system 415 transports the containers 300 held within their individual caddie 200. The UV lamp module 410 can define the sterilization zone within the antechamber 405. The sterilization zone includes the space within the antechamber within which the container 300 is positioned for full exposure to the flash lamps 430. The UV radiation sources may be directed upward, downward, and/or from the sides, alone or in combination with an opposing UV radiation source. In an implementation, a first UV flash lamp module 410 is positioned under the transport system 415 holding the container 300 and a second UV flash lamp module 410 is positioned above the transport system 415 holding the container 300. The sterilization zone in this implementation can be defined as the space between the first and second UV flash lamp modules 410 where the container 300 is positioned to be sterilized. The UV flash lamps 430 can simultaneously or sequentially expose all surfaces inside the antechamber 405 including the caddie 200 and the container 300. In an implementation, the UV lamp modules 410 can include xenon lamps. Xenon lamps are electric arc lamps designed to produce extremely intense, incoherent, full-spectrum light (e.g., 200 nm-1200 nm) for very short durations. The glass envelope is commonly made of fused quartz, borosilicate, Pyrex, or other UV transparent material. The spectrum is rich in UV-C light (e.g., between 200-280 nm, or between 180 nm and 300 nm).

Each UV flash lamp 430 can be sealed from the portion of the antechamber 405 containing the caddies 200 holding the containers 300 positioned on the transport system 415 by a barrier 460. In an implementation, a first barrier 460 is positioned under the transport system 415 separating a first UV flash lamp 430 from the transport system 415 and a second barrier 460 is positioned over the transport system 415 separating the second UV flash lamp 430 from the transport system 415. The barriers 460 can be UV-transparent or opaque and hermetically-sealed.

Figure 4:
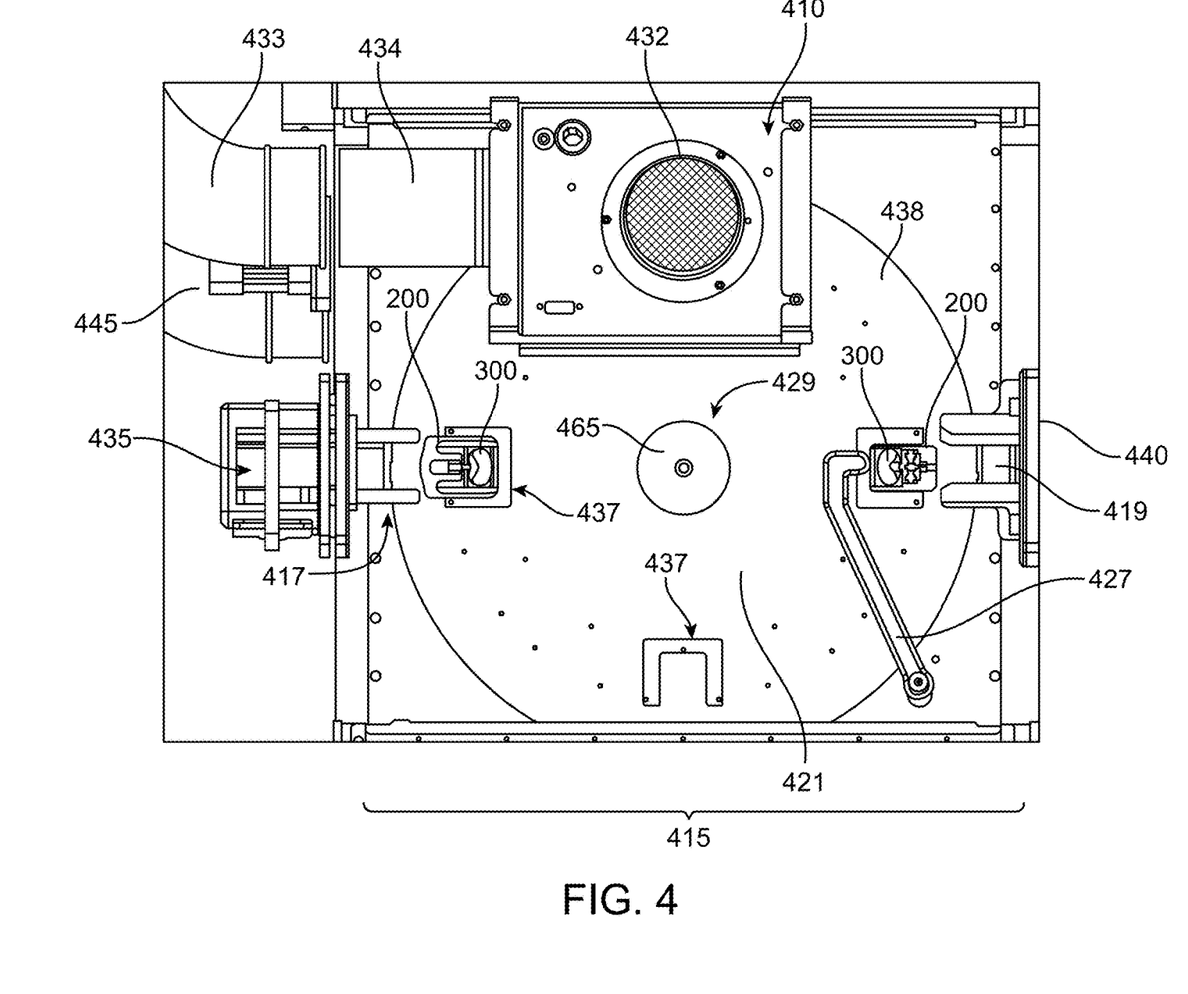
FIG. 4 is a top-down, partial view of the sterilization system of FIG. 3.

FIGS. 3 and 4 show the transport system 415 inside the antechamber 405. The transport system 415 is configured to transport each caddie 200 loaded with a container 300 into, within, and/or out from the antechamber 405. The transport system 415 can include an inlet chute 417 and a turntable 421 positioned inside the antechamber 405. The inlet chute 417 is configured to receive each caddie 200 as it enters the antechamber 405 through the inlet box and door 435. The caddie 200 can slide on the chute 417 towards the turntable 421 located inside the antechamber 405. As discussed above, a loading conveyor 15 (identified in FIG. 1A) can be used that is configured to transfer each caddie 200 into the sterilization system 400 through the inlet box and door 435 (see FIG. 2). The loading conveyor 15 can be arranged so that each caddie approaches the inlet door 435 of the antechamber 405 and is received by the inlet chute 417 to be directed toward the turntable 421. The turntable 421 of the transport system 415 can be a round, planar structure configured to receive and support each caddie 200 on its upper surface 438 upon receipt of the caddie 200 within the antechamber 405. The turntable 421 can include a central region and a perimeter region surrounding the central region. The caddies 200 are received within the perimeter region of the turntable 421. The perimeter region of the turntable 421 supporting the caddies 200 is preferably formed of a UV transparent material as described elsewhere herein. In some implementations, both the perimeter region and the central region of the turntable 421 are formed of a UV transparent material.

The turntable 421 can be mounted to a rotary base 429 that couples the turntable 421 to a motor 431 (see FIG. 3). The motor 431 can be an electric motor, such as a stepper motor, servo motor, continuous motor, and the like. The motor 431 can be a brushless DC motor or any type of motor or drive suitable for rotating a shaft. The motor 431 can be a position-control DC motor with integrated driver and controller. The motor 431 can be programmed to have variable speeds and/or multiple rotations upon activation. In some implementations, the motor 431 is an electric motor that incorporates gear reduction via a gear box or other mechanism. The turntable 421 can incorporate a keying feature so that the turntable 421 does not slip or lose orientation relative to the motor 431 as it moves. For example, the turntable 421 can include an off-center hole, which in conjunction with center hole/screw serves as keying feature.

The transport system 415 need not incorporate a round turntable 421 configured to rotate around a central axis by the motor 431. The transport system 415 can incorporate a single conveyor belt configured to move the caddies 200 linearly through the antechamber between the pulsed UV lamps 430. Where the transport system 415 is described as incorporating a turntable that rotates around an axis, the transport system can optionally include a belt or other transport system that moves linearly upon actuation of the motor 431. Various configurations of the moving/conveying mechanisms are considered herein.

The motor 431 can move the turntable 421 so that caddies 200 received within a first region of the turntable 421 from the inlet chute 417 can travel inside the antechamber 405 into position between the pulsed-UV lamps 430 and further towards the outlet chute (not shown) after sterilization. The material of the turntable 421 or the portion of the turntable 421 configured to hold the caddies 200 allows UV light to pass through and is UV transparent. Long wave UV (UV-A) has wavelength that is between about 315 and 400 nm and passes easily through both plastic and glass. Short wave UV (UV-C) has a wavelength that is between 100 to 280 nm and is most effective in killing bacteria. However, short wave UV cannot pass through ordinary glass or most plastics. In an implementation, the portion of the turntable 421 that supports the caddies 200 is formed of a material that is transparent to all wavelengths of UV (UV-A, UV-B, and UV-C). The turntable 421 material that supports the caddies 200 can include and be composed of cyclical olefin copolymers (COC), fused quartz or fused silica glass, high-silica glass, or other specialized UV glass compositions. In an implementation, the turntable 421 material is highly homogeneous, chlorine-free, synthetic fused silica glass for UV optical applications in the deep ultraviolet and visible spectrums (e.g., below 180 nm-2000 nm) such as SUPRASIL UVL (Heraeus, Buford, GA), GE® 124 fused quartz glass made from crystalline silica (Swift Glass, Elmira, NY), Corning® HPFS 7980 fused silica (Canton, NY), Tosoh® ES (Tosoh Global, South San Francisco, CA).

The rotary base 429 positioned near the central axis of the turntable 421 away from the location of the caddies 200 need not be transparent to UV and can be formed of materials, such as metal. The metal rotary base 429 can be positioned centrally and the UV transparent portion of the turntable 421 can surround the central rotary base 429 so that the outer region of the turntable 421 is fully UV transparent. The caddies 200 holding the containers 300 are positioned on this fully UV transparent region of the turntable 421 so that all surfaces of the caddie 200 and the container 300 are exposed to the UV light from the lamps 430 above and below the turntable 421. The UV clear turntable 421 allows for pulsed-UV light exposure from under the turntable 421 to reach the caddies/containers positioned on the upper surface of the turntable 421. The barriers 460 can be positioned within an interior of the antechamber 405 to separate the turntable 421 from the UV lamp modules 410. These barriers 460 or portions thereof are UV-transparent material as well. For example, the barrier 460 can be stainless steel and incorporate a UV-transparent window.

The components of the sterilization system 400 that are near the container 300 being sterilized by the UV are preferably UV transparent so that no shadows are formed on the container 300 so that the container 300 is suitably sterilized. The caddies 200 and at least a portion of the transport system 415, and at least a portion of the containers 300 can all be fully UV transparent. In some implementations, only a portion of the container 300 is UV transparent, which will be discussed in more detail below. The various components of the sterilization system 400, such as gaskets, seals, cushioning components, washers, and the like can be UV-resistant or hardened silicone materials.

The antechamber 405 can incorporate one or more reflective surfaces in order to redirect a substantial fraction of the light towards the container 300 held in a caddie 200 on the turntable 421. One or more UV light reflectors 465 or mirrors within the antechamber 405 can sample the UV light pulses and redirect it to one or more light sensors, which can measure the light and communicate the data for use in the control module 425. The light reflector 465 is shown in FIGS. 3 and 4 as a polished upper surface of the rotary base 429 as an example. The position of the reflector(s) 465 can vary. The UV reflectors can make sure enough reflected light is present for the light sensor. The reflectors can be panels fabricated from quartz, glass, aluminum, coated aluminum, and/or stainless steel or the like. The reflectors can be coated, partially coated, and/or multiply coated with at least one reflective material, such as, for example a monochromatic wavelength specific dielectric coating and/or material. Examples of suitable monochromatic wavelength specific dielectric coatings and/or materials include, without limitation, silicon dioxide, hafnium dioxide and the like. In an implementation, the reflectors is a MAG-fluoride coated aluminum. The reflectors can have any of a variety of geometries, dimensions, sizes, or numbers. In an implementation, the reflectors can form a mosaic of reflectors to maximize UV light on the container 300 while minimizing any shadows. The reflectors can be positioned near the location of the caddie 200/container 300 positioned on the transport system 415 within the antechamber 405 or an interior wall of the antechamber 405 near the transport system 415. This positioning of the reflectors ensure that it is in a location representative of the intensity of the UV light at the container 300, but that it does not block UV light exposure of the container 300. The UV light sensors are configured to monitor the intensity and/or relative changes in the pulsed-UV light during operation of the sterilization system 400.

Figure 5:
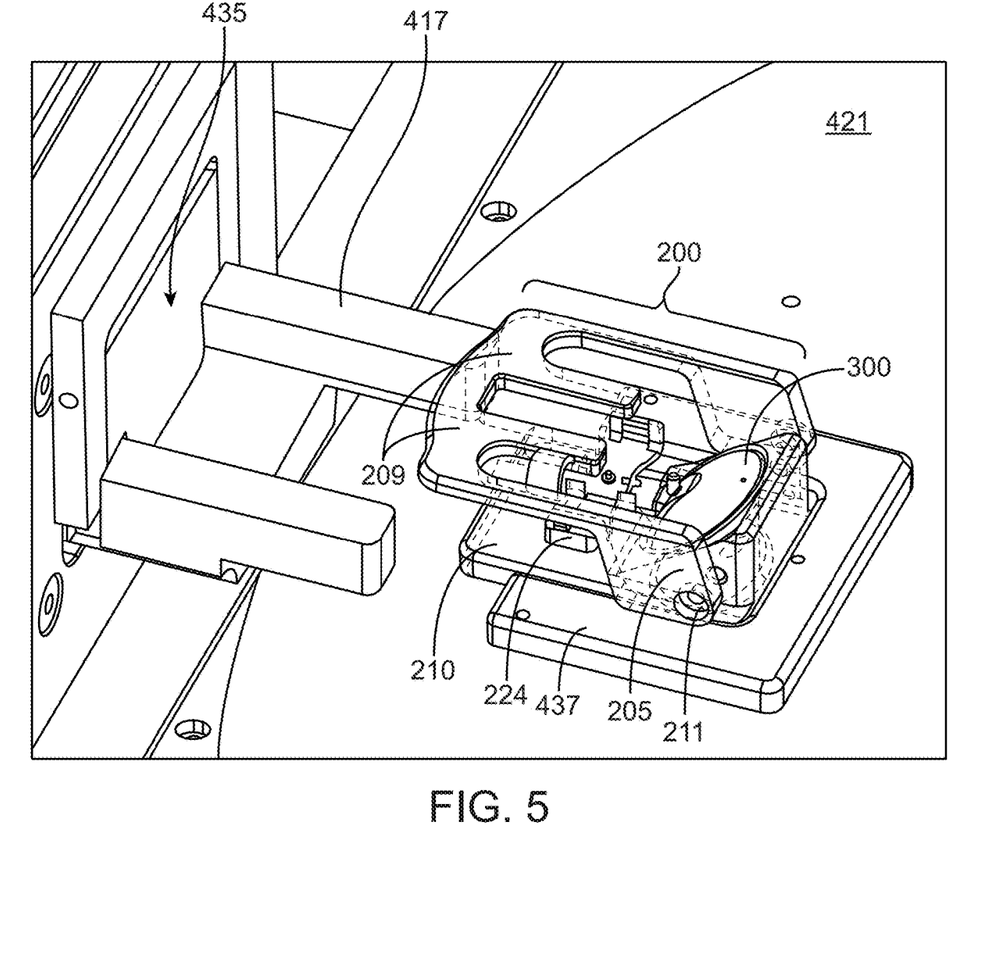
FIG. 5 is a partial view of an implementation of a transport system of the sterilization system of FIG. 4 with a caddie positioned on the turntable.

Again with respect to FIGS. 3 and 4, the turntable 421 can incorporate one or more positioning features 437 on its upper surface 438 for receiving each caddie 200 and to prevent the caddies 200 from sliding too far onto the turntable 421 from the inlet chute 417. The positioning features 437 can arrange each caddie 200 on the turntable 421 so that the caddie 200 will be appropriately positioned for exposure to the UV lamps 430. In an implementation, the turntable 421 is a circular disc configured to receive the caddies 200 on an outer region of the upper surface 438 of the turntable 421. The positioning features 437 can project from the upper surface 438 a distance away from the outermost perimeter of the turntable 421 to define a maximum distance each caddie 200 can slide onto the upper surface 438 from the chute 417. The positioning features 437 can have a shape complementary to a shape of the caddie 200 so that the caddie 200 can be received within the positioning feature 437 (see also FIG. 5). This allows for the caddies 200 to achieve a desired position on the upper surface 438 of the turntable 421 that is suitably aligned with the UV lamps 430. The positioning features 437 are also UV clear to avoid casting any shadows on the caddie 200 or the container 300 being sterilized.

The UV-transparent turntable 421 can be mechanically- or magnetically-coupled to the sealed rotary base 429. The indexing sensors can be configured to stop motion of the turntable 421 once the caddie 200 is positioned accordingly prior to activating the lamps 430.

The transport system 415 can include a pneumatic actuator 423 configured to move each caddie 200 following sterilization from the turntable 421 onto an outlet chute 419 (see FIG. 4). The outlet chute can be positioned inside the isolator 500 so that the caddie 200 first exits the antechamber 405 via the outlet door 440 before sliding down the outlet chute. A caddie divert gate 427 driven by the pneumatic actuator 423 can transfer each caddie 200 from the turntable 421 onto the outlet chute so it may be directed into the isolator 500. The caddie divert gate 427 can be static or active and mounted, for example, inside of the antechamber 405.

The air handling system 420 can include a suction blower to provide air-cooling within the antechamber 405 of the lamps and/or the antechamber 405 as well as to exhaust ozone that may be generated within the antechamber 405. Each UV flash lamp 430 can incorporate a cooling air inlet 432 and a cooling air exhaust port 434 coupled to suction tube 433 (see FIG. 3). Where the UV lamp module 410 incorporates a pair of UV flash lamps, a first suction tube 433 can connect to the cooling air exhaust port 434 of the first UV flash lamp 430 and a second suction tube 433 can connect to the cooling air exhaust port 434 of the second UV flash lamp 430. Elbow flanges 436 can be mounted through the walls of the antechamber 405 to provide connectors for each of the suction tubes 433. A fan unit within the xenon light enclosure can focus flow onto any hot spots.

The input air may be filtered to prevent particles from getting into the antechamber 405 and/or the UV lamp thereby increasing bulb life and efficiency. The output air may also be filtered to deactivate ozone or other gasses accumulated within the antechamber 405. Thus, the cooling air within the suction tubes 433 can run through one or more filters. The filters can be activated carbon filters that catalytically deactivate any ozone generated by the UV lamps 430. Removal of the ozone protects the drugs upon filling of the container 300. The air handling system 420 can incorporate one or more sensors to monitor airflow and shut down the system of inadequate airflow is detected.

The air handling system 420 may monitor, record, and/or regulate temperature, humidity, and/or composition. The temperature control may include forced air heating or cooling, fluid-filled heat exchangers, radiant heating, and the like. In some embodiments, composition of gas in the chamber may be controlled, for example, by selectively introducing one or more gasses (e.g., nitrogen) to catalyze reactions, neutralize toxic byproducts, and/or clean or otherwise sanitize the environment in an antechamber 405. In some embodiments, visible (e.g., colored) gasses may be introduced to assess laminar flow, detect seal integrity, etc.

. . . within the respective chambers. In some embodiments, desiccants and/or adsorbents may be used to control the environment in the chamber.

The air handling system 420 can incorporate horizontal laminar airflow with a fan-powered HEPA filter element 450 that can blow HEPA air from the back of the antechamber 405 to a single-pass air exit near a front of the antechamber 405. This blows exhaust from the antechamber 405 out through a second passive exhaust HEPA filter element (not shown). Thus, HEPA-filtered "first air" can flow horizontally across the container 300 held within the caddie 200 inside the antechamber 405 with the HEPA filter element serving as a sterile air vent.

The sterilization system 400 can include electronics, such as a main controller and one or more additional controllers in a distributed network architecture. The main controller may provide supervisory and management of operations and coordinate the performance of sub-operations by the other controllers. Each controller may include one or more processors that perform operations according to software that may be developed, and compiled using one or more languages. The controllers may be in the form of embedded systems, having dedicated controllers, PLCs (programmable logic controllers), PC-based controllers with appropriate networking and I/O hardware and software, ASICs, or other implementations.

Figure 1D:
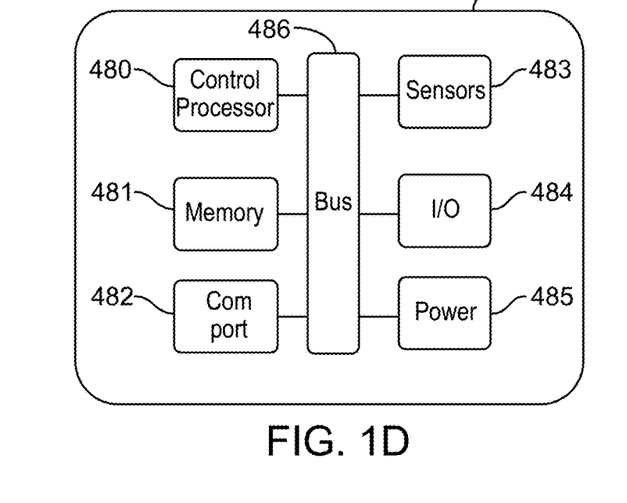
FIG. 1D is a box diagram of an implementation of a control module for the sterilization system of FIG. 1C.

The sterilization system 400 can include a control module 425 (see FIG. 1D). The control module 425 can include a control processor 480, memory 481, a COM port 482, one or more sensors 483, one or more input/outputs 484 ports, power 485, and the like. The various components of the control module 425 can be interconnected via a system bus 486. The control processor 480 can be used to supervise, monitor, and control operations according to programmed instructions and/or hardware configurations (e.g., analog, digital, PAL, and/or ASIC circuits).

The sterilization system control processor 480 can be in operative communication with one or more of the other electrical components of the system 10 to process instructions for execution within the system 10 and such executed instructions can implement one or more of the processes described herein related to the use of the system 10. The control processor 480 can be a single-threaded processor or a multi-threaded processor. The control processor can be capable of processing instructions stored in the memory 481 and/or on a storage device to provide an output of information to the user about operation of the system 10. The control processor 480 can include software capable of being programmed. The software run by the control processor 480 can provide certain aspects of the system 10 without any user input during use. In an implementation, the adjustments or programming can be via the control processor 480 that is controlled by software.

The control processor 480 can communicate with or otherwise control operation of the transport system 415, the UV lamp module 410, the air handling system 420, the sensors 483, the input/output 484 ports, the memory 481, and the like. The control processor 480 can also include programming configured to control one or more components of the sterilization system 400. For example, the control processor 480 may include circuitry to control timing of the transport system 415 relative to the state of UV lamp module 410 and/or the air handling system 420. The control processor(s) 480 can include programming that allows the processor(s) to receive signal and/or other data from an input device, such as a sensor or other input of the system 10. The processors 480 may receive the signals, for example, from a sensor or a transmitter/receiver on the caddie 200 and/or container 300 and store the signals in the memory 481. The control system 480 may be linked to the transport system 415 to control/maintain the speed of the containers 300 moving through the sterilization zone. For example, the transport system 415 can be maintained at a constant speed or operated at variable speeds to achieve a particular exposure with respect to the UV lamp module 410 within the sterilization zone. The speed at which the containers 300 are moved to and/or through the sterilization zone may be adjusted so as to achieve the desired energy treatment level based on, for example, a desired residence time/exposure time of each container within the sterilization zone. The control system may also control and/or modify the process parameters (e.g., UV wavelength, UV intensity, etc.) so as to affect a desired sterilization result, and such processing parameters may be adjusted/selected (either alone or in combination with the rate/residence time of the container systems/products within the treatment zone/exposure tunnel) to achieve desired sterilization results.

The control processor 480 circuitry may include one or more clocks (oscillators), charging circuitry, I/O controllers, memory, etc. Alternatively or in addition, the circuitry of the control processor 480 may include circuitry for one or more wireless communication modes, including Bluetooth, near-field communication (NFC), WiFi, ultrasound, ZigBee, RFID, etc.

The control processor 480 can also be in operative communication with one or more external computing devices. The external computing device can vary including, but not limited to, desktop computer, laptop computer, tablet computer, smartphone, or other device capable of communicating and receiving user input.

The memory 481 may be part of the control processor 480 or otherwise in data communication with the control processor 480. The memory 481 is configured for receiving and storing user input data. The memory 481 can be configured to store user information, history of use, verification of containers, and the like. The memory 481 can be any type of memory capable of storing data and communicating that data to one or more other components of the system 10, such as the control processor 480. The memory 481 may be one or more of a Flash memory, SRAM, ROM, DRAM, RAM, EPROM, dynamic storage, and the like. The size of the memory 481 can vary as is known in the art.

The COM port 482 may be serial or parallel, and may use packet or non-packet based communication protocols (e.g., RS-232, USB, Firewire) to receive and/or send signals to a master controller.

The I/O port 484 can be used to receive and send signals to the sensors 483 and/or other components (e.g., motor, lamps) in the system 400. The control module 480 may send and/or receive status and control information to or from a host computer or controller via the COM port 482. The input/outputs 484 may be combined or the input may be separate from the output. The one or more input/outputs 484 can include one or more triggers, buttons, sliders, dials, keypads, switches, touchscreens, or other input that can be retracted, pressed, squeezed, slid, tapped, or otherwise actuated to activate, modify, or otherwise cause a response of the system. The input/outputs 484 can be one or more indicator lights that can provide, for example, information about status or power of system 10.

The sensors 483 can also include temperature, smoke, contaminant, vibration, position, light intensity sensors, airflow, accelerometers, motion sensors, capacitive sensors, flow sensors, or the like. These sensors can detect user handling and interaction, position of containers within the antechamber, opening and closing of the inlets and outlets, etc. The sensors 483 can include a UV light sensor that measures the light intensity of the UV light in the antechamber 405 to monitor the sufficiency of the light pulses. Sensors 483 may be used to monitor the condition of the bulb and the intensity of the flash. The sensors 483 may also be used to confirm the appropriate light dose has been delivered, for example, an average minimum threshold over multiple pulses. A sensor 483 (e.g., light beam, proximity, or contact) may be included within the antechamber 405 to monitor the position or proximity of the container 300 (and/or caddie 200). A sensor 483 may be used to monitor the position or proximity of the container and provide an interlock such that the bulb cannot flash if the container is not in the correct position. As discussed above, the turntable 421 can be moved (e.g., rotated or linearly through the antechamber) by the motor 431. The sensors 483 can include indexing sensors for discreet positioning of each caddie 200 relative to the UV lamps 430. Information from the one or more sensors 483 in the system can be communicated to an interface that converts the measured signals from the various sensors 483 and transmits the information to the control processor 480 of the sterilization system 400.

The one or more input/outputs 484 can be optical (LED, display), tactile (e.g. vibrational, etc.), sonic (e.g. speaker, etc.), or the like. The one or more input/outputs 484 can also be more elaborate, such as a GUI having an input. The type of visual output/display may include LCD displays, LED displays, plasma displays, OLED displays and the like. The output/display may also be an interactive or touch sensitive screen having an input device, such as a touch screen, a capacitance screen, a resistive screen or the like. The one or more input/outputs 484 can also include a vibratory motor, speaker, warning, alarm, alert, clock, timer, or other features.

Power 485 can be supplied to one or more components of the system 10 and/or the control processor 480. The power supply 485 can drive the UV lamps during a pulse. The power supply 485 may store energy in a capacitor, inductor, or in resonant (L-C) circuit, for example. In response to a trigger signal, the stored energy may be released to the flash lamp, such as a Xenon flash tube, for example.

In some implementations, the system 10 can incorporate a communication module 482 in operative communication with one or more components of the system, such as the control processor 480, as well as with one or more peripheral devices, such as one or more external computing devices. The connection between the components of the sterilization system 400 can include a wired communication port, such as a RS232 connection, USB, Fire wire connections, proprietary connections, or any other suitable type of hard-wired connection configured to receive and/or send information. The communication can also include a wireless communication port such that information can be fed to/from the system via a wireless link. The wireless connection can use any suitable wireless system, such as Bluetooth, Wi-Fi, radio frequency, ZigBee communication protocols, infrared, or cellular phone systems, and can also employ coding or authentication to verify the origin of the information received. The wireless connection can also be any of a variety of proprietary wireless connection protocols.

Drug Container

The primary container 300 for sterilization using the sterilization system 400 can vary in its configuration, including a vial, bag, cartridge, syringe, or other receptacle designed to hold one or more doses of a therapeutic. The sterilization system 400 can be used with any of a variety of primary containers 300 and should not be limited to the particular container 300 described herein. The disclosed systems and methods may be used for sterilization of beverage and/or food products and/or their containers, medicines and/or their containers, pharmaceuticals and/or their containers, vitamins and/or their containers, infusion products and/or their containers, clinical and/or non-clinical solutions/systems and/or their containers, enteral and/or parenteral solutions/systems and/or their containers, and the like.

The primary container 300 being sterilized is preferably constructed or at least partially constructed of a UV-transparent material so that germicidal UV light can pass through the material of the primary container 300 from at least one angle, and preferably more than a single direction. As discussed above, the UV module has preferably two UV flash lamps positioned above and below the caddie 200 holding the container 300 on the turntable 421. The caddie 200 and the container 300 are formed of UV-transparent materials so that the UV waves are able to pass through them and sterilize the reservoir formed by the container 300. Example materials for the container 300 include cyclical olefin copolymers.

In an aspect, the primary container 300 is a sub-assembly of a device designed to deliver microdoses of a therapeutic including the device described in U.S. Application Publication No. 2021/0177650, published Jun. 17, 2021, which is incorporated by reference here in its entirety.

The container 300 can have any suitable shape and size configured for receiving a medicament. Generally, the container 300 is sized large enough to contain multiple doses. The container 300 can be rigid walled, expandable, or a combination thereof. In some implementations, an interior capacity of the container 300 is about 1 ml to about 10 ml, more specifically, about 1.5 ml to about 5 ml, or about 1.75 ml to about 3 ml, or about 2.5 ml, or about 3 ml. Any of a variety of medicaments can be contained within the container 300 following sterilization as described in more detail below.

Figure 6A:
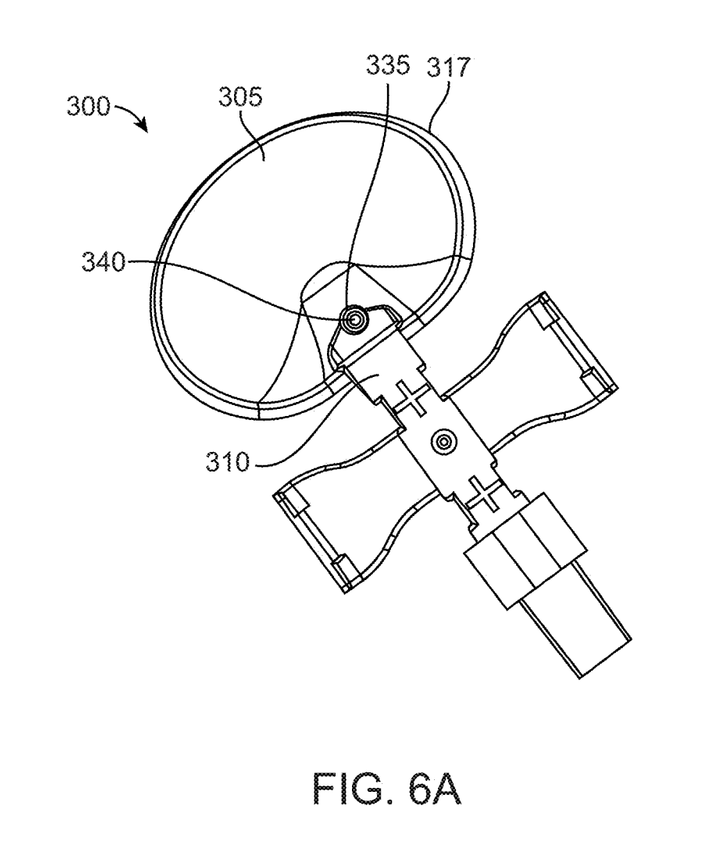
FIGS. 6A-6B are front and back perspective views of an implementation of a container for sterilization.
Figure 6B:
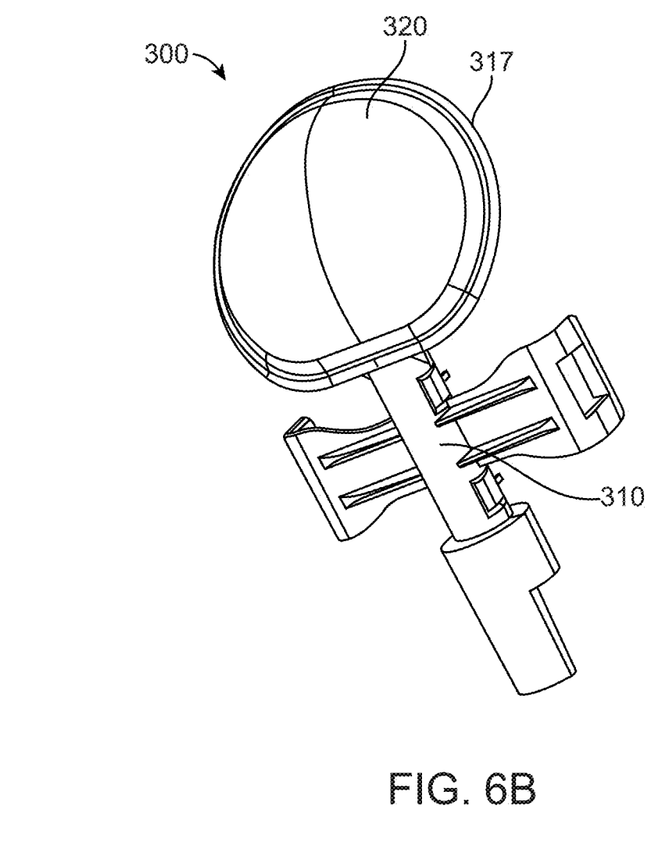

FIGS. 6A-6B illustrate an implementation of a primary container 300 suitable for use with the sterilization system 400 described herein. The container 300 can include a reservoir manifold 305 that together with the reservoir film 320 defines, at least in part, a reservoir portion having an internal volume for containing the medicament. The container 300 also includes on a lower end region a pump manifold body 310. The pump manifold body 310 defines an inner bore configured to receive a pump configured to draw and eject doses medicament from the internal volume formed within the reservoir manifold 305 and reservoir film 320. The reservoir manifold 305, the reservoir film 320, and the pump manifold body 310 together form the primary container 300 that can be sterilized using the systems described above.

The reservoir film 320 allows for the container 300 to be expandable/collapsible. The reservoir manifold 305 can be positioned on a first side (FIG. 6A) and the reservoir film 320 on a second, opposite side (FIG. 6B). The reservoir manifold 305 can have a concave inner surface and a mating edge 317 at an outer perimeter of the concave inner surface. The edge 317 is configured to mate with a corresponding outer perimeter of the reservoir film 320. The reservoir film 320 can be a collapsible foil, film, or membrane that is relatively thin. The reservoir film 320 can be non-compliant or compliant. For example, the film 320 can have a thickness of about 0.001 inch to about 0.030 inch, more specifically about 0.002 inch to about 0.004 inch. The reservoir manifold 305 can be relatively rigid and/or unmovable. The reservoir film 320 tents outward or collapses inward depending on how much fluid is contained within the internal volume. Filling the reservoir with a material can cause the reservoir film 320 to tent, expand, enlarge, or otherwise move outwards away from the reservoir manifold 305. As the material in the reservoir is consumed, the reservoir film 320 may collapse back down towards the reservoir manifold 305. The reservoir film 320 may be expandable and collapsible such that it moves relative to the reservoir manifold 305, but is generally not elastic or stretchy. The reservoir film 320 of the reservoir means that no venting is necessary during use. The collapse of the reservoir film 320 towards the manifold 305 is what makes up for the volume of drug removed from the container during each cycle. It should be appreciated, however, that the system may include venting in the manifold 305 to allow air to escape. This venting can aid in eliminating any air bubbles from entering the drug reservoir. As an example, venting of the reservoir can be accomplished via a one-way valve allowing air to escape the reservoir, but not enter the reservoir. The reservoir film 320 features very low vapor transmission rates to prevent drug evaporation prior to, and during product use.

Any of a variety of materials can be used for the reservoir manifold 305 and the pump manifold body 310. The material(s) is preferably UV-transparent and allows germicidal UVC wavelengths to pass through as described elsewhere herein. In an implementation, the reservoir manifold 305, the pump manifold body 310, and optionally the reservoir film 320 are formed of cyclic olefin co-polymer (COC) (CAS No. 26007-43-2). The material of the reservoir film 320 can vary, but is generally a flexible, non-permeable material with good vapor barrier. The materials of the reservoir manifold 305, the pump manifold body 310, and the reservoir film 320 may be selected based on their biocompatibility, stability, sterility, and whether or not they are extractable/leachable. The reservoir film 320 can, but need not be UV-transparent. For example, the manifold body 310 can be UV-transparent and the reservoir film 320 is not UV-transparent. So long as at least one of the components forming the reservoir (e.g., the reservoir film 320 or the manifold body 310) is UV-transparent the light can enter the reservoir for sterilization. Any UV transparent material is considered herein, and is preferably compatible for heat melting, RF welding, etc., between components. In some implementations, the reservoir film 320 can be made from polymers, such as PET, SiO, linear low density polyethylene or the like. In some implementations, the reservoir film 320 is a metalized plastic film or foil suitable for drug containment including flexible aluminum foil/Polyolefin film. The reservoir film 320 can be multilayered and formed of more than a single material. For example, the reservoir film 320 can have a layer that is not UV transparent and another layer, such as the portion that contacts the reservoir manifold, that is UV transparent (e.g., made of COC).

Again with respect to FIG. 6A, the container 300 can incorporate a fill port 335 located near the lower end region of the reservoir manifold 305. The fill port 335 can be penetrated by a needle or similar tool configured to inject fluid into the reservoir without damaging the container 300. The fill port 335 can be sealed by one of, but not limited to, a plug, cap, heat cut/seal, or other sealing element 340. In some implementations, the container 300 can include more than a single port. For example, a first port can be configured for filling the container and a second port can be configured for venting, such as for airing out the container following sterilization.

Caddie

The sterilization system 400 described herein is configured to be used with one or more caddies 200 configured to hold securely the primary containers 300 during sterilization as well as other aseptic processing steps of the container 300 including USON leak testing and fill and finish steps within the isolator 500. The caddie 200 therefore provides accurate positioning and mechanical support for the container 300, such as during fill and finish within the isolator 500, while minimizing handling of the container 300, particularly near the sterile fill port 335. The caddie 200 can be formed of a dimensionally stable, UV-transparent material as can the reservoir surfaces of the container 300, including the reservoir manifold 305, the pump manifold body 310, and the reservoir film 320, so that both can be UV-sterilized as described elsewhere herein. In an implementation, the caddie 200 is cyclic olefin co-polymer (COC) (CAS No. 26007-43-2). The caddie 200 additionally maximizes the area for unobstructed access of pulsed-UV to the container 300 and minimizes or eliminates shadows on the container 300 thereby providing for the maximum array of UV light to substantially every surface of each container 300 while in the sterilization zone.

Figure 7:
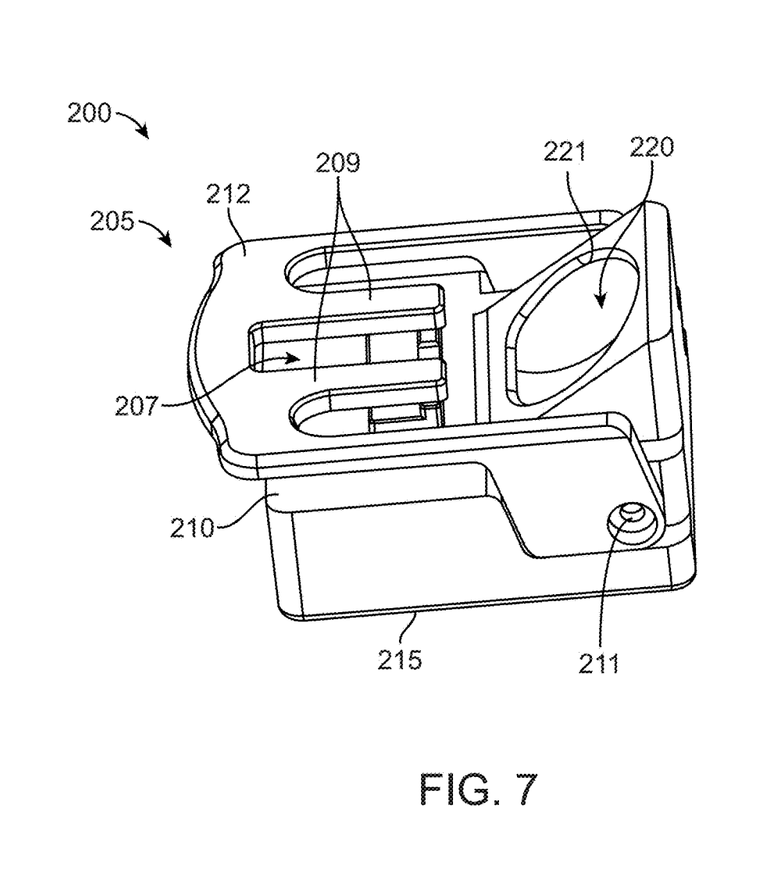
FIG. 7 shows a perspective view of an implementation of a caddie having a latch.
Figure 8:
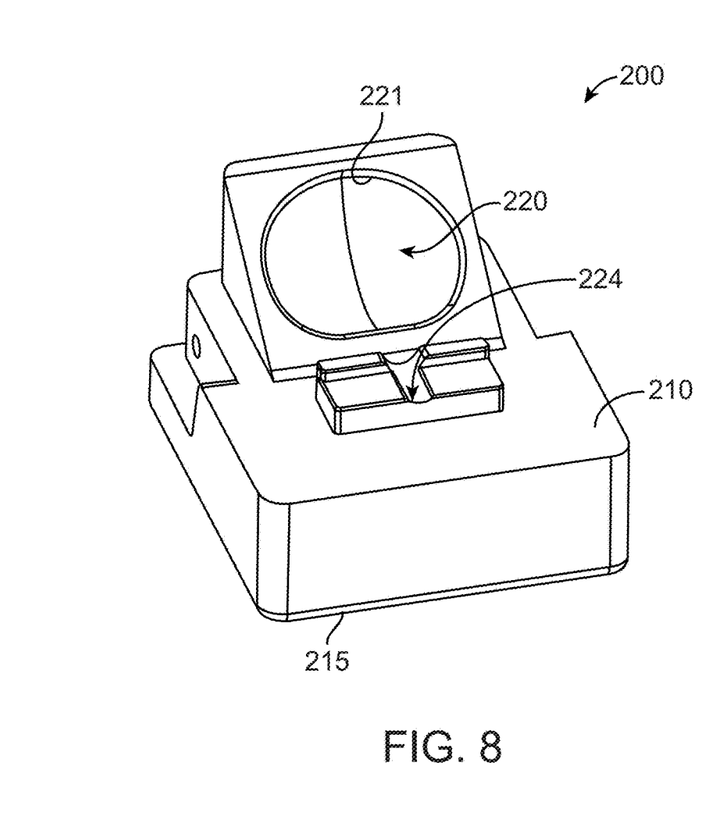
FIG. 8 shows a perspective view of the caddie of FIG. 7 with the latch removed.

The caddie 200 is designed to have a shape complementary to the container 300 being processed. FIGS. 7 and 8 illustrate an implementation of a caddie 200 having a particular shape configured to hold the shape of the container 300 shown in FIGS. 6A-6B. Other complementary arrangements are considered herein.

The caddie 200 can include an upper surface 210 and a lower surface 215. The lower surface 215 is configured to be positioned against the upper surface 438 of the turntable 421. The lower surface 215 can have a shape that corresponds substantially to the upper surface 438 of the turntable 412 on which it is positioned. The lower surface 215 can define a perimeter sized to be received within a space defined by the positioning feature 437 on the upper surface 438 of the turntable 412. The upper surface 210 of the caddie 200 is configured to mate with at least a portion of the container 300. The upper surface 210 can define a shape that corresponds substantially to the portion(s) of the container 300 it supports. In an implementation, the upper surface 210 of the caddie 200 can include a nest 220 sized and shaped to mate with the reservoir portion of the container 300 shown in FIG. 6A-6B. The nest 220 can be a depression in the upper surface 215 that has a depth and an outer perimeter 221 sized and shaped to receive the edge 317 of the reservoir manifold 305 of the container 300. The container 300 can be placed film-side 320 down within the nest 220 of the caddie 200. The caddie 200 can include further surface features 224 in its upper surface 210 sized and shaped to receive at least another portion of the container 300. For example, a pump manifold body 310 extending from the reservoir manifold 305 can be received, at least in part, within surface feature 224 sized and shaped to mate with the pump manifold body 310 when the reservoir manifold 305 sits within nest 220. The nest 220 and any other mating surface features 224 of the caddie 200 are shaped to receive a container 300 such that the container is held along a particular orientation and/or angle relative to the upper surface 210 that is suitable for handling and securing the container. FIGS. 7 and 8 provide just one example of a caddie 200 for mating with the supporting a container 300. The shape, size, and configuration of both the caddie 200 and the container 300 can vary and should not be limited to just this one arrangement.

The caddie 200 can additionally incorporate a latch 205 movable with respect to the upper surface 210 (FIG. 7). The latch 205 can be coupled to the caddie 200, such as by a hinge 211, so that the latch 205 can be articulated away from the upper surface 210 to reveal the nest 220 for loading of a container 300 within the nest 220 and articulated towards the upper surface 210 over the loaded container 300 to secured and retain the container 300 within the nest 220 of the caddie 200. The latch 205 can have any of a variety of configurations in order to retain the container 300. In an implementation, the latch 205 can have a central channel 207 forming first and second fingers 209 that are positioned on either side of the pump manifold body 310 of the container 300 once positioned within the depression 224. The latch 205 can have a portion 212 opposite the hinge 211 that extends beyond a perimeter of the upper surface 210 to aid a user in opening the latch 205. The latch 205 can have a snap fit over the container 300 providing the user with audible or tactile feedback regarding the securement of the container 300 within the nest 220.

Operational Sequence

A user can insert a container 300 within a caddie 200 so that the reservoir film 320 is positioned face-down within the nest 220. The latch 205, if present, can be articulated down over the container 300 to hold the container 300 relative to the nest 220. The container 300 can be leak tested prior to sterilization. The caddie 200 holding the container 300 can be loaded onto a loading conveyor 15 to transfer each caddie 200 towards the inlet 435 of the sterilization system 400. The caddie 200 can enter the antechamber 405 of the sterilization system 400 by sliding down the inlet chute 417 towards the turntable 421. The caddie 200 can be received within one of the positioning features 437 on the upper surface 438 of the turntable 421. The turntable 421 can rotate to transfer the caddie 200 positioned within the positioner 437 from the inlet chute 417 into alignment between the UV lamps 430 for sterilizing with pulsed-UV light. Once UV-sterilized, the caddie 200 on the turntable 421 can be rotated until the caddie 200 contacts the divert gate 427 and is moved out the door 440 onto the exit chute to the isolator 500. Once inside the isolator 500, the caddie 200 can be placed onto a carriage of the fill and finish equipment 100. The container 300 can be evacuated and filled with a solution, sealed, and returned to its position on the caddie 200. The caddie 200 and/or container 300 can be removed from the carriage of the fill and finish equipment 100 from within the isolator 500 and placed onto a chute to slide out of the isolator 500 into the post-chamber 600. The container 300 can be removed from the caddie 200, inspected, and tested for dimensions. Acceptable units can be placed into protective bulk packing tray. The caddie 200 can be placed onto a return conveyor so the caddie 200 is available for reuse in leak testing with another container 300 to be sterilized. One or more of the steps of the operational sequence can be performed by robotic equipment automatically or manually by one or more operators.

Aspects of the subject matter described herein may be realized in digital electronic circuitry, integrated circuitry, specially designed ASICs (application specific integrated circuits), computer hardware, firmware, software, and/or combinations thereof. These various implementations may include an implementation in one or more computer programs that are executable and/or interpretable on a programmable system including at least one programmable processor, which may be special or general purpose, coupled to receive signals, data and instructions from, and to transmit signals, data, and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any computer program product, apparatus, and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" or "lower" or "downwards" may indicate a first direction away from a reference point. Similarly, "proximal" or "upper" or "upwards" may indicate a location in a second direction opposite to the first direction. However, such terms are provided to establish relative frames of reference, and are not intended to limit the use or orientation of the device to a specific configuration described in the various implementations.

The word "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. An in-line sterilization system comprising:
a container comprising a reservoir portion defining an internal volume;
a caddie sized and shaped to releasably secure the container; and
a sterilization system comprising:
a first light source and a second light source forming a sterilization zone between the first and second light sources, each of the first and second light sources configured to transmit pulsed ultraviolet light into the sterilization zone; and
a transport system comprising a turntable having a perimeter region configured to support the caddie and move the caddie through the sterilization zone,
wherein the reservoir portion, the caddie, and at least the perimeter region of the turntable are transparent to the ultraviolet light to sterilize the container prior to the internal volume being filled with a pharmaceutical.

2. The system of claim 1, wherein the ultraviolet light has a wavelength of between 200 nm and 400 nm.

3. The system of claim 1, further comprising a container-filling isolator, wherein the sterilization system is incorporated in-line and upstream of the container-filling isolator.

4. The system of claim 1, wherein the first light source is positioned above the turntable and the second light source is positioned below the turntable.

5. The system of claim 1, wherein the caddie is formed of cyclic olefin co-polymer.

6. The system of claim 1, wherein the perimeter region of the turntable is formed of fused silica glass.

7. The system of claim 1, wherein the container is formed of cyclic olefin co-polymer.

8. The system of claim 1, wherein the reservoir portion of the container comprises a reservoir manifold sealed to a reservoir film, wherein at least one of the reservoir manifold and the reservoir film comprises cyclic olefin co-polymer.

9. The system of claim 1, wherein the caddie comprises a nest formed in an upper surface of the caddie that is sized and shaped to mate with the reservoir portion of the container.

10. The system of claim 9, wherein the upper surface of the caddie further comprises a surface feature sized and shaped to mate with a manifold coupled to the reservoir portion.

11. The system of claim 10, wherein the caddie further comprises a latch configured to articulate relative to the upper surface of the caddie to secure the container within the nest.

12. An in-line sterilization system comprising:
a caddie sized and shaped to releasably secure a container; and
a sterilization system comprising:
an antechamber;
a first light source and a second light source positioned within the antechamber and forming a sterilization zone between the first and second light sources, each of the first and second light sources configured to transmit pulsed ultraviolet light into the sterilization zone; and
a transport system comprising a turntable having a perimeter region, the perimeter region of the turntable arranged to support the caddie upon receipt of the caddie within the antechamber, the turntable configured to move the caddie supported on the perimeter region through the sterilization zone,
wherein the caddie and at least the perimeter region of the turntable are transparent to the ultraviolet light.

* * * * *